US012440421B1

(12) United States Patent
Chowansky

(10) Patent No.: US 12,440,421 B1
(45) Date of Patent: Oct. 14, 2025

(54) SHOCKWAVE THERAPY CHAMBER

(71) Applicant: Nolan Chowansky, Bluffton, SC (US)

(72) Inventor: Nolan Chowansky, Bluffton, SC (US)

( * ) Notice: Subject to any disclaimer, the term of this patent is extended or adjusted under 35 U.S.C. 154(b) by 0 days.

(21) Appl. No.: 19/082,605

(22) Filed: Mar. 18, 2025

(51) Int. Cl.
*G16H 20/40* (2018.01)
*A61H 23/00* (2006.01)

(52) U.S. Cl.
CPC ........... *A61H 23/008* (2013.01); *G16H 20/40* (2018.01); *A61H 2201/0111* (2013.01); *A61H 2201/0115* (2013.01); *A61H 2201/0169* (2013.01); *A61H 2201/0176* (2013.01); *A61H 2201/5007* (2013.01); *A61H 2201/5043* (2013.01); *A61H 2201/5064* (2013.01); *A61H 2201/5082* (2013.01); *A61H 2203/02* (2013.01); *A61H 2230/20* (2013.01); *A61H 2230/50* (2013.01)

(58) Field of Classification Search
CPC ............................ A61H 23/008; G16H 20/40
USPC ............................................................. 606/1
See application file for complete search history.

(56) References Cited

U.S. PATENT DOCUMENTS 9,956,374 B2 5/2018 Hoefler
2015/0346810 A1* 12/2015 Urbach .................. G06F 3/013
345/501
2019/0015624 A1 1/2019 Hill et al.

FOREIGN PATENT DOCUMENTS

WO WO-2023094913 A1 * 6/2023 ............ G06F 3/017

* cited by examiner

*Primary Examiner* — Nadia A Mahmood

(57) ABSTRACT

A shockwave therapy system integrating sensory deprivation and artificial intelligence-controlled treatment delivery is disclosed. The system may comprise a sensory deprivation chamber containing a body of water in which a patient floats while receiving shock wave therapy. The therapy may be delivered through multiple robotic arms that may be controlled by an AI system which may optimize treatment parameters in real-time. The system may incorporate an Infinitus Omni Remote Sensor System mounted above the patient that may monitor vital signs through radar-based monitoring, infrared thermometry, and remote pulse oximetry. The monitoring data may be displayed to medical practitioners and may be integrated into the AI's treatment optimization protocols. This integrated approach may provide a method for delivering shock wave therapy in a controlled, floating environment while maintaining continuous patient monitoring and automated treatment optimization.

14 Claims, 8 Drawing Sheets

SHOCKWAVE THERAPY CHAMBER

BACKGROUND OF THE INVENTION

1. Field of the Invention

The present invention relates to shockwave therapy chambers and, more particularly, to a shockwave therapy chamber that integrates sensory deprivation flotation with AI-controlled robotic delivery of shock wave therapy and continuous non-contact vital sign monitoring.

2. Description of the Related Art

Several designs for shockwave therapy inventions have been designed in the past. None of them, however, include the integration of sensory deprivation flotation, AI-guided robotic shock wave delivery, and non-contact vital sign monitoring in a single therapeutic system.

Applicant believes that a related reference corresponds to U.S. patent application publication No. 20190015624, which discloses an inflatable water floatation tank which can be used for therapeutic sensory deprivation sessions. Applicant believes that another related reference corresponds to U.S. Pat. No. 9,956,374, which discloses an isolation chamber which forms a soundproof enclosure in which the user floats in water. None of these references, however, teach of a shockwave therapy chamber that is comprised of a sensory deprivation chamber which contains a body of water in which the user floats upon while receiving directed shock wave therapy from a plurality of robotic arms that are controlled by an AI computer system which optimizes the treatment regime. Shockwave therapy in water is more effective, as water facilitates its propagation.

Other documents describing the closest subject matter provide for a number of more or less complicated features that fail to solve the problem in an efficient and economical way. None of these patents suggest the novel features of the present invention, namely a full-body shockwave therapy powered by artificial intelligence (AI)

SUMMARY OF THE INVENTION

It is one of the objects of the present invention to provide a shockwave therapy chamber that combines multiple therapeutic modalities to address a wide range of conditions, from muscle, joints, tendon, and the entire musculoskeletal system injuries.

It is another object of this invention to provide a shockwave therapy chamber that incorporates AI to ensure that each treatment is tailored to the patient's specific needs, thereby improving outcomes.

It is still another object of the present invention to provide a shockwave therapy chamber, wherein its sensory deprivation environment promotes deep relaxation, which can enhance the body's natural healing processes.

It is yet another object of this invention to provide such a device that is inexpensive to implement and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which.

DETAILED DESCRIPTION OF THE EMBODIMENTS OF THE INVENTION

Figure 1:
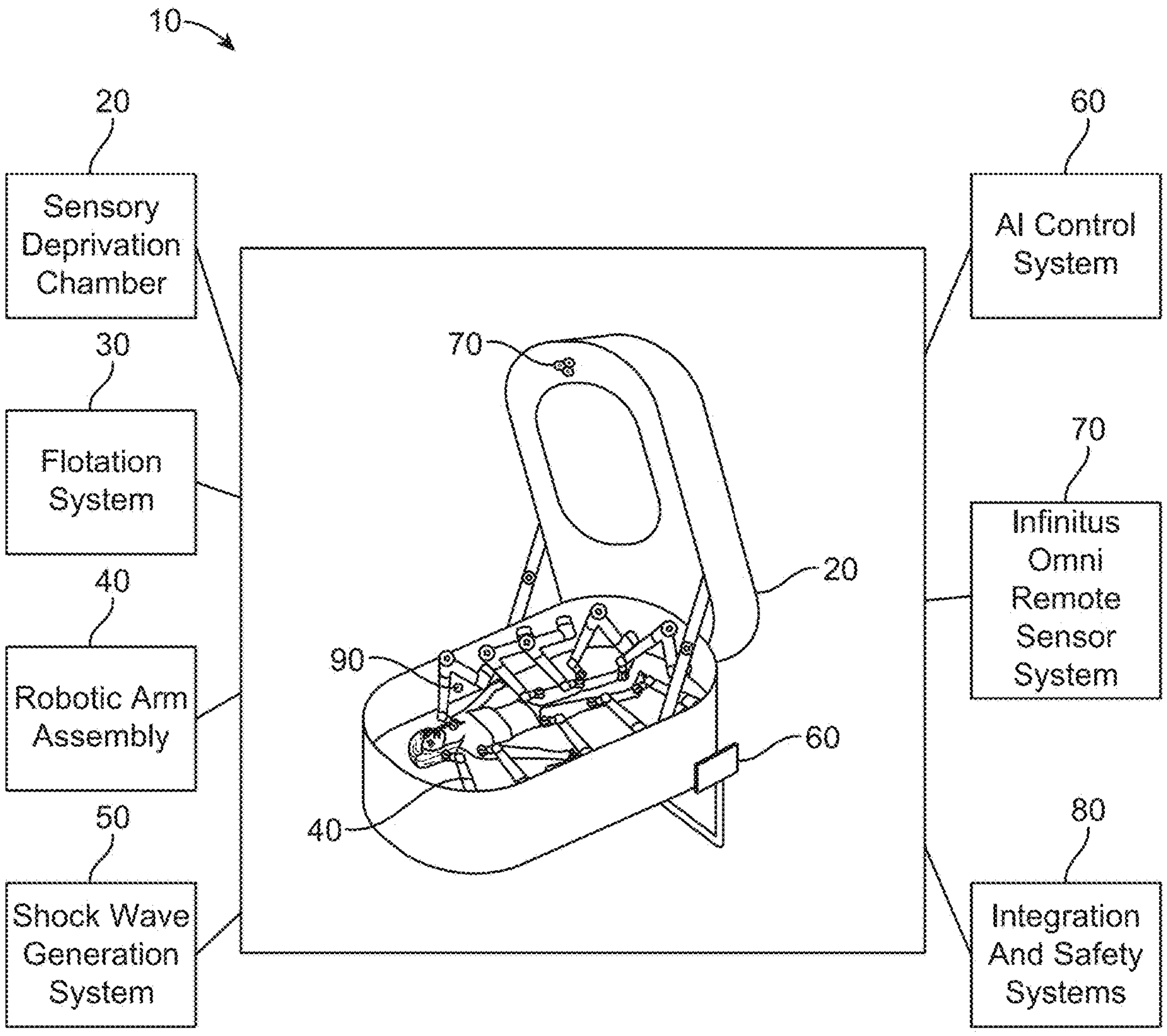
FIG. 1 represents a front perspective view of the present invention according to an exemplary embodiment thereof.
Figure 2:
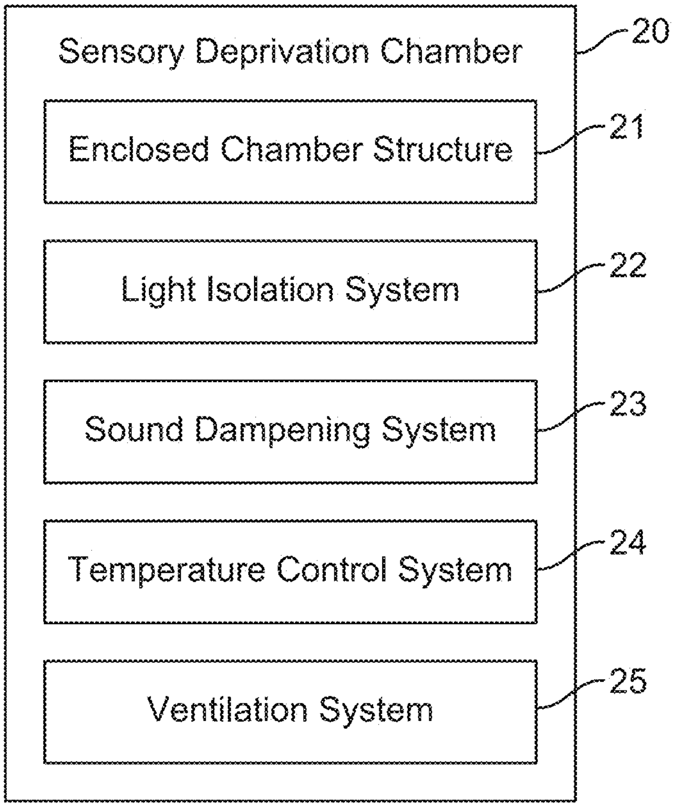
FIG. 2 shows a block diagram of the sensory deprivation chamber according to an embodiment thereof.
Figure 3:
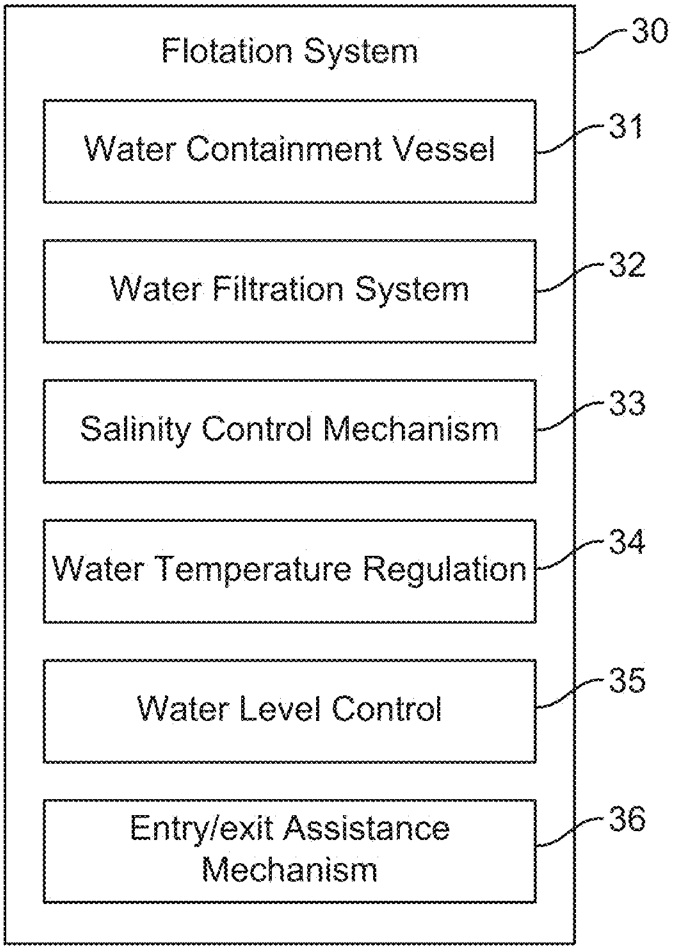
FIG. 3 illustrates a block diagram of the flotation system according to an embodiment thereof.
Figure 4:
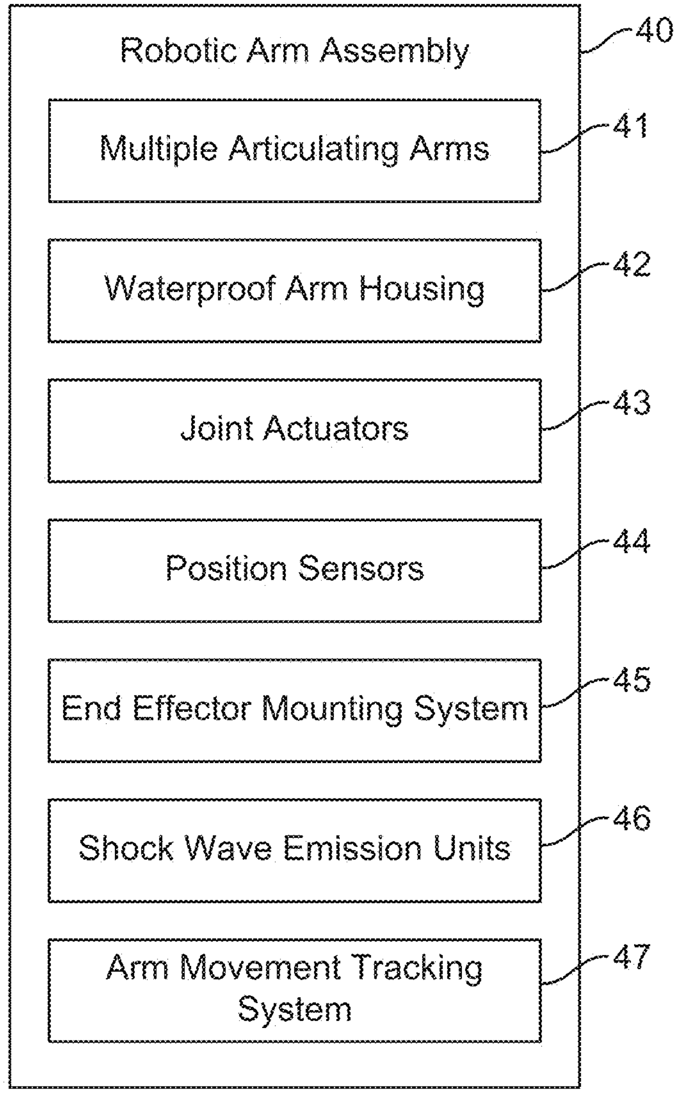
FIG. 4 is a representation of a block diagram of the robotic arm according to an embodiment thereof.
Figure 5:
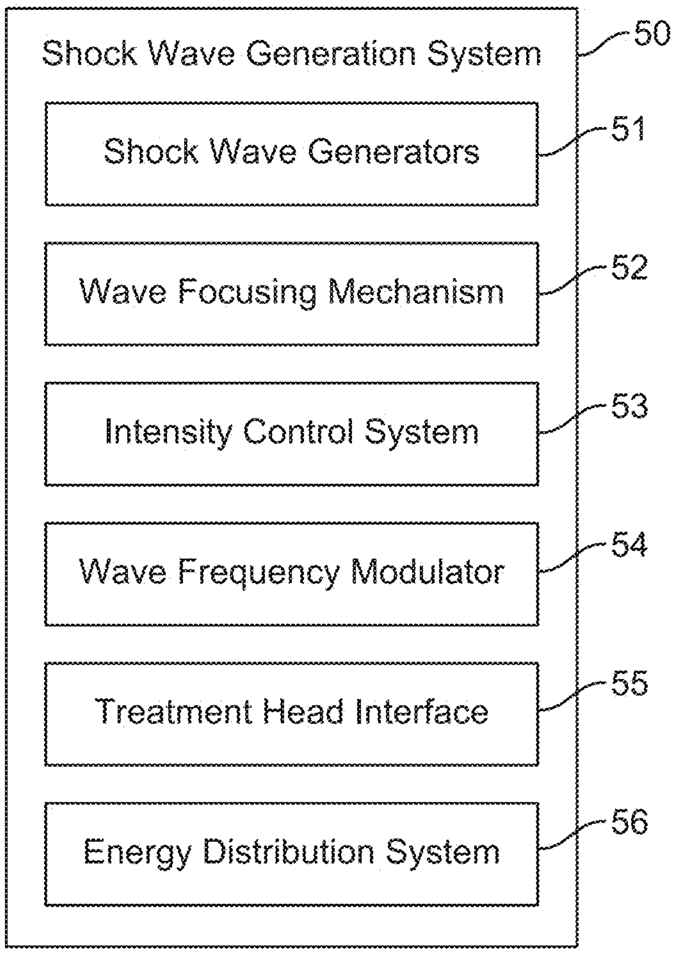
FIG. 5 shows a block diagram of the shock wave generation system according to an embodiment thereof.
Figure 6:
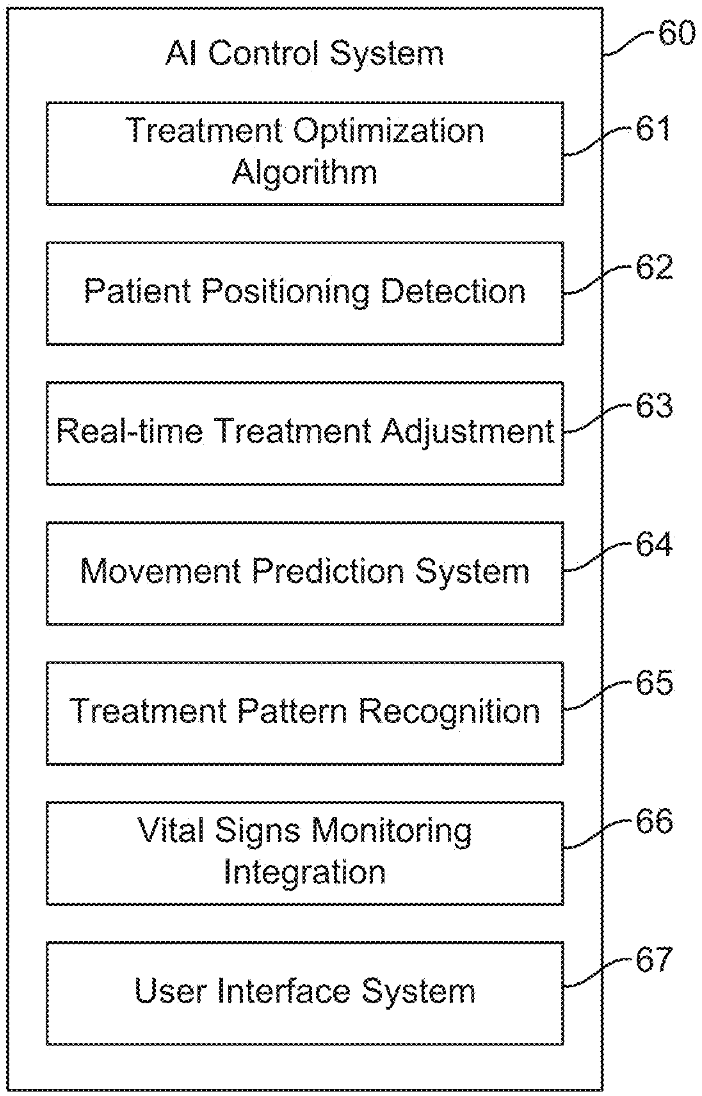
FIG. 6 illustrates a block diagram of the artificial intelligence (AI) control system according to an embodiment thereof.
Figure 7:
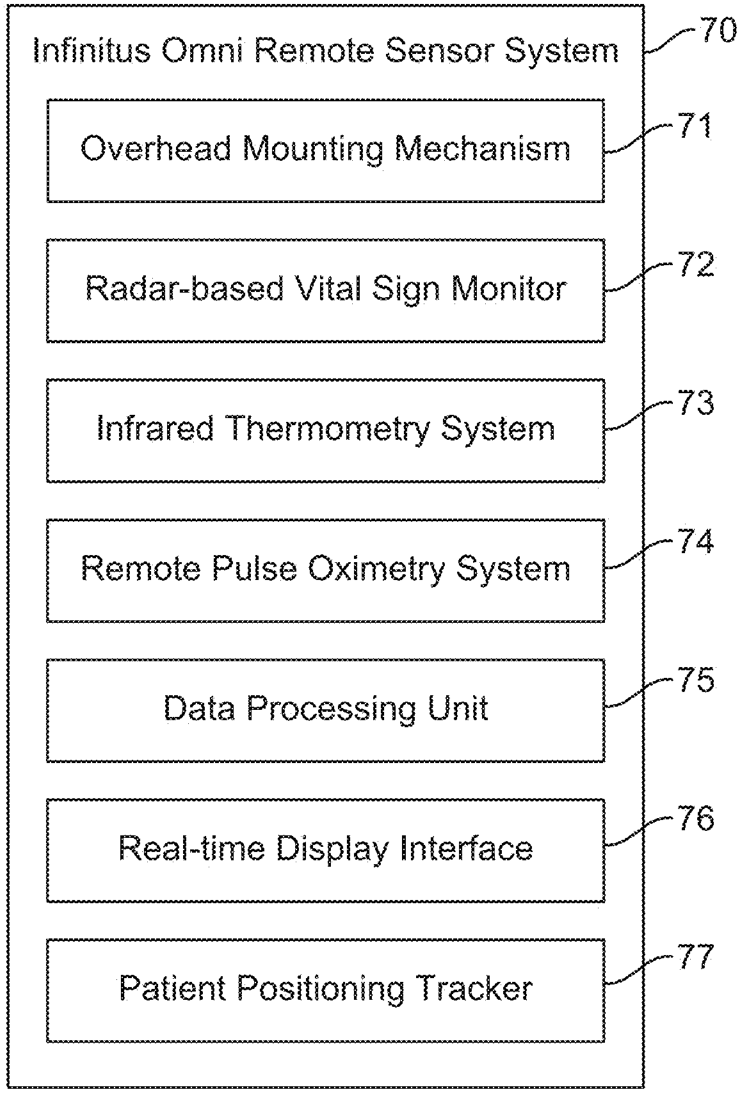
FIG. 7 is a representation of a block diagram of the infinitus omni remote sensor system according to an embodiment thereof.
Figure 8:
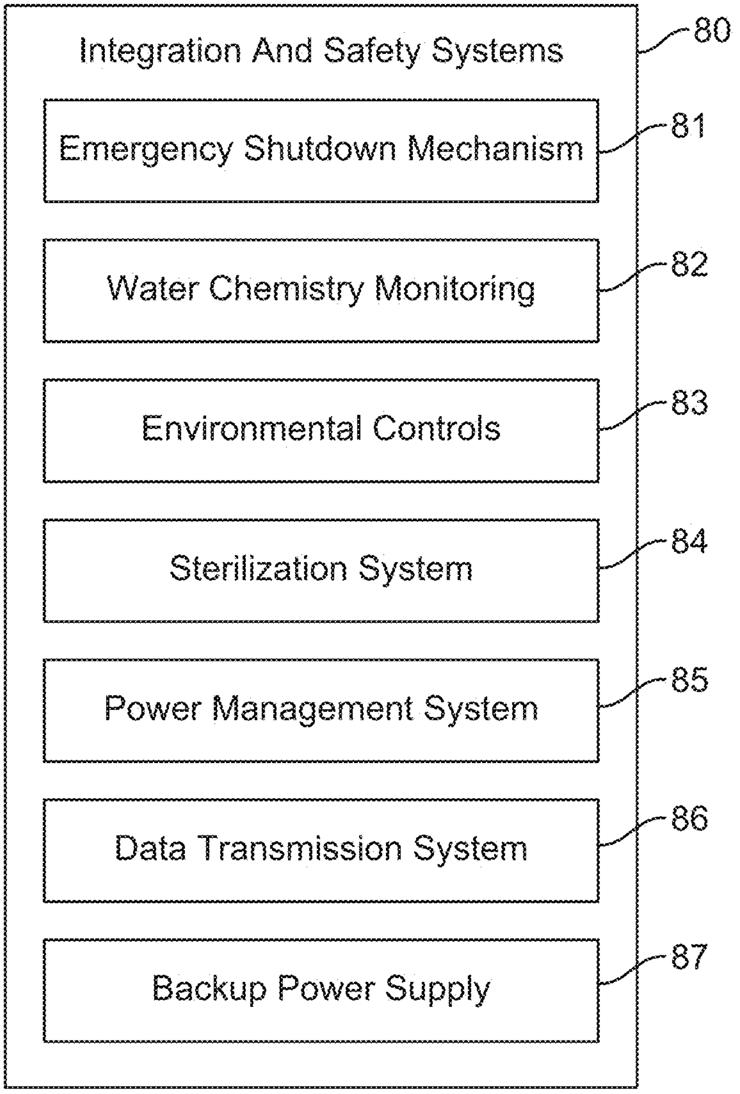
FIG. 8 shows a block diagram of the integration and safety system according to an embodiment thereof.

In accordance with the present invention, a shockwave therapy system is provided that integrates sensory deprivation and AI-controlled treatment delivery. The following detailed description outlines various embodiments of the invention with reference to the accompanying elements and their respective numerals.

The sensory deprivation chamber (20) forms the primary housing of the invention, comprising an enclosed chamber structure (21) designed to minimize external stimuli. The chamber structure incorporates a light isolation system (22) and sound dampening system (23) to create an optimal environment for treatment. A temperature control system (24) maintains stable ambient conditions, while an entry/exit assistance mechanism (25) facilitates safe patient ingress and egress. The sensory deprivation chamber assembly (20) may be constructed in several configurations to achieve the desired sensory isolation while accommodating the specialized requirements of shock wave therapy delivery. The enclosed chamber structure (21) may be fabricated using medical-grade stainless steel, fiber-reinforced polymer composites, or high-density polyethylene (HDPE). The chamber walls may be formed as a double-wall construction, where the interstitial space may be filled with sound-dampening material. Alternatively, the walls may be constructed using prefabricated panels with tongue-and-groove connections sealed with medical-grade silicone gaskets.

The light isolation system (22) may comprise a light-tight door seal utilizing industrial-grade neoprene or EPDM rubber gaskets, along with a mechanically interlocked entrance vestibule that may prevent direct light penetration. The interior surfaces may feature specialized light-absorbing coatings such as matte black elastomeric compounds, and the system may include a programmable LED ambient lighting system with dimming capabilities for controlled environment manipulation.

Sound isolation through the sound dampening system (23) may be achieved through the installation of mass-loaded vinyl barriers within wall cavities and the application of acoustic foam panels. The system may incorporate a floating floor construction utilizing vibration-isolating mounts and may implement acoustic seals around all penetrations and joints. An optional active noise cancellation system utilizing strategically placed speakers and microphones may be implemented for enhanced sound isolation.

Environmental regulation through the temperature control system (24) may be accomplished via an integrated HVAC system and a humidity control system. Temperature sensors may be placed at multiple points within the chamber, working in conjunction with an air circulation system designed for minimal noise generation. Heat exchangers may be incorporated for water temperature maintenance, ensuring optimal conditions for both the patient and the equipment.

The entry/exit assistance mechanism (25) may feature hydraulic or pneumatic-assisted door operation and non-slip surfaces on all walking areas. The system may include grab bars constructed of medical-grade stainless steel and emergency release mechanisms operable from both inside and outside the chamber. Built-in steps or ramp may be included to ensure accessible entry and exit for all patients.

The chamber assembly (20) may incorporate various integration features to accommodate system components. These may include reinforced mounting plates for robotic arm assembly (40) attachment points, waterproof electrical conduits for power and control systems, plumbing connections for water management, and data cable pathways for sensor and control systems. The chamber design may specifically include overhead mounting provisions for the Infinitus Omni Remote Sensor System (70).

The flotation system (30) includes a water containment vessel (31) designed to accommodate a single patient in a floating position. A water filtration system (32) maintains water purity, while a salinity control mechanism (33) ensures optimal buoyancy. Water temperature regulation (34) and water level control (35) systems work in concert to maintain consistent floating conditions. The entry/exit assistance mechanism (36) enables safe patient transitions. The water containment vessel (31) may be constructed using materials suitable for medical applications, which may include medical-grade stainless steel, reinforced acrylic, or specialized composite materials. The vessel may incorporate curved or ergonomic contours to enhance patient comfort and may feature structural reinforcements to accommodate the integration of therapy delivery systems.

The water filtration system (32) may be implemented through various filtration technologies that may include mechanical, chemical, and ultraviolet purification stages. The system may incorporate automated backwashing capabilities and may feature bypass circuits for maintenance operations. The filtration components may be designed for easy access and replacement, potentially incorporating quick-disconnect fittings and modular filter housings.

A salinity control mechanism (33) may be incorporated to maintain optimal flotation conditions. This mechanism may include automated salt concentration monitoring devices and dispensing systems. The mechanism may feature continuous monitoring capabilities and may include provisions for automatic or manual adjustment of solution density. The system may incorporate storage reservoirs for concentrated saline solution and may include mixing chambers for homogeneous distribution.

The water temperature regulation system (34) may utilize heat exchange technology that may include multiple heating and cooling elements. The system may incorporate temperature sensors at various points within the vessel and may feature redundant temperature control mechanisms. The regulation system may be designed to respond to both ambient temperature fluctuations and therapeutic requirements.

Water level control (35) may be achieved through various mechanisms that may include automated level sensing and adjustment systems. The control system may incorporate overflow protection features and may include provisions for automated water addition or removal. The system may be designed to maintain optimal water levels during patient entry and exit, potentially incorporating compensation for displacement variations.

The entry/exit assistance mechanism (36) may be designed to facilitate safe patient transition between dry and floating states. This may include various support structures that may be mechanical, hydraulic, or pneumatic in nature. The mechanism may feature adjustable components to accommodate different patient requirements and may incorporate non-slip surfaces and support handles. The system may be designed to operate in both normal and emergency scenarios and may include provisions for assistance personnel access when required.

The robotic arm assembly (40) comprises multiple articulating arms (41) housed in waterproof enclosures (42). Each arm features precision joint actuators (43) and position sensors (44), with an end effector mounting system (45) supporting shock wave emission units (46). An arm movement tracking system (47) ensures precise positioning during treatment. In one embodiment, the robotic arms may include shockwave therapy means.

The waterproof arm housing (42) may be constructed using materials suitable for prolonged exposure to the aqueous environment. The housing may incorporate various sealing technologies that may include gaskets, O-rings, or mechanical seals. The housing design may feature modular construction to facilitate maintenance and may include provisions for pressure equalization to prevent water ingress.

The joint actuators (43) may utilize various drive technologies that may include servo motors, hydraulic systems, or pneumatic mechanisms. The actuators may be designed to provide precise movement control and may incorporate feedback mechanisms for position verification. The system may include provisions for torque limiting and may feature emergency stop capabilities.

The position sensors (44) may be implemented using various sensing technologies that may provide real-time feedback about the spatial orientation of each arm segment. The sensing system may incorporate redundant measurement capabilities and may feature self-calibration functionality. The sensors may be designed to maintain accuracy in the aquatic environment and may include provisions for drift compensation.

The end effector mounting system (45) may be designed to accommodate various shock wave emission units and may incorporate quick-change capabilities. The mounting system may feature standardized interfaces to allow for different treatment heads and may include provisions for automatic tool identification. The system may incorporate various locking mechanisms to ensure secure attachment during operation.

The shock wave emission units (46) may be integrated into the arm assembly through specialized mounting interfaces. These units may be designed for optimal energy transfer in the aquatic environment and may include various focusing mechanisms. The emission units may incorporate cooling provisions and may feature adjustable parameters for treatment customization.

The arm movement tracking system (47) may utilize various technologies to monitor and control the position and movement of all robotic arms simultaneously. The system may incorporate collision avoidance capabilities and may feature predictive movement algorithms. The tracking system may be designed to coordinate multiple arms in real-time and may include provisions for treatment zone mapping.

The shock wave generation system (50) incorporates advanced shock wave generators (51) with a sophisticated wave focusing mechanism (52). An intensity control system (53) modulates treatment strength, while the wave frequency modulator (54) adjusts treatment parameters. The treatment head interface (55) and energy distribution system (56) ensure optimal shock wave delivery. In different embodiments, the generators may utilize electrohydraulic, electromagnetic, or piezoelectric principles, or combinations thereof. The system may be designed to produce waves of varying characteristics and may include provisions for rapid adjustment of generation parameters.

The wave focusing mechanism (52) may employ various technologies to direct and concentrate the generated shock waves. The mechanism may incorporate adjustable focusing elements that may include reflectors, lenses, or arrays. The focusing system may be designed to provide variable focal lengths and may include provisions for beam shaping to accommodate different treatment requirements.

The intensity control system (53) may utilize various methods to modulate the energy output of the shock wave generators. The system may incorporate multiple stages of energy control and may feature both coarse and fine adjustment capabilities. The control mechanism may be designed to provide consistent output levels and may include provisions for real-time energy monitoring.

The wave frequency modulator (54) may be implemented through various technologies to adjust the temporal characteristics of the shock wave delivery. The modulator may incorporate timing control systems and may feature variable frequency capabilities. The system may be designed to provide precise timing control and may include provisions for burst pattern generation.

The treatment head interface (55) may be designed to efficiently couple the generated shock waves to the aqueous environment. The interface may incorporate various matching layers and may feature adjustable coupling mechanisms. The system may include provisions for monitoring coupling efficiency and may be designed to maintain optimal energy transfer under varying conditions.

The energy distribution system (56) may utilize various technologies to manage the delivery of power to the shock wave generators. The system may incorporate power conditioning capabilities and may feature surge protection mechanisms. The distribution system may be designed to provide stable power delivery and may include provisions for rapid energy storage and release.

The AI control system (60) operates through a treatment optimization algorithm (61) that continuously monitors patient positioning (62) and enables real-time treatment adjustments (63). The system includes movement prediction capabilities (64), treatment pattern recognition (65), vital signs monitoring integration (66), and a comprehensive user interface system (67).

The treatment optimization algorithm (61) may incorporate various computational methods to manage and refine therapy delivery. The algorithm may utilize machine learning techniques that may adapt to individual patient responses and may include provisions for pattern recognition and predictive modeling. The system may be designed to continuously refine treatment parameters and may incorporate various optimization strategies.

The patient positioning detection system (62) may employ various sensing technologies to monitor the patient's location and orientation within the treatment chamber. The detection system may incorporate multiple sensor types and may feature real-time tracking capabilities. The system may be designed to maintain accurate position information and may include provisions for motion compensation.

The real-time treatment adjustment mechanism (63) may utilize various technologies to modify treatment parameters during therapy sessions. The mechanism may incorporate feedback loops from multiple sensor systems and may feature rapid response capabilities. The system may be designed to make nuanced adjustments to therapy delivery and may include provisions for both automated and manual intervention.

The movement prediction system (64) may employ various algorithmic approaches to anticipate patient movement patterns. The system may incorporate historical data analysis and may feature predictive modeling capabilities. The prediction mechanism may be designed to enhance treatment accuracy and may include provisions for real-time trajectory adjustment.

The treatment pattern recognition system (65) may utilize various analytical methods to identify and categorize therapeutic responses. The system may incorporate multiple data streams and may feature pattern matching capabilities. The recognition system may be designed to identify optimal treatment patterns and may include provisions for therapeutic protocol refinement.

The vital signs monitoring integration (66) may employ various technologies to incorporate physiological data into treatment decisions. The integration system may incorporate multiple vital sign parameters and may feature real-time analysis capabilities. The system may be designed to maintain comprehensive patient monitoring and may include provisions for automated response to physiological changes.

The user interface system (67) may utilize various technologies to facilitate interaction between medical professionals and the treatment system. The interface may incorporate multiple display modalities and may feature intuitive control mechanisms. The system may be designed to provide comprehensive treatment information and may include provisions for both routine operation and emergency intervention.

The Infinitus Omni Remote Sensor System (70) is mounted at the top of the chamber via an overhead mounting mechanism (71). This system integrates radar-based vital sign monitoring (72), infrared thermometry (73), and remote pulse oximetry (74) capabilities. A dedicated data processing unit (75) processes physiological data, while a real-time display interface (76) presents information to medical practitioners. The patient positioning tracker (77) ensures optimal sensor alignment.

The overhead mounting mechanism (71) may incorporate various structural elements designed to support and position the sensor array at the top of the treatment chamber in a downward-facing orientation directed toward the patient, focusing on the carotid artery, forehead, and chest. The mounting system may utilize adjustable brackets and may feature vibration-dampening capabilities. The mechanism may be designed to maintain precise sensor alignment for continuous patient monitoring and may include provisions for service access while maintaining optimal positioning above the treatment area.

The radar-based vital sign monitor (72) may employ various electromagnetic sensing technologies to detect physiological parameters. The monitoring system may incorporate multiple radar frequencies and may feature advanced signal processing capabilities. The system may be designed to penetrate the aqueous environment and may include provisions for motion artifact compensation.

The infrared thermometry system (73) may utilize various thermal detection technologies to monitor patient temperature. The system may incorporate multiple sensing elements and may feature environmental compensation capabilities. The thermometry system may be designed to provide continuous temperature monitoring and may include provisions for rapid response detection.

The remote pulse oximetry system (74) may employ various optical technologies to measure blood oxygen saturation. The system may incorporate multiple wavelength analysis and may feature advanced signal processing capabilities. The oximetry system may be designed to function in the specialized environment and may include provisions for movement compensation.

The data processing unit (75) may utilize various computational technologies to analyze and integrate sensor data. The processing system may incorporate multiple analysis algorithms and may feature real-time processing capabilities. The unit may be designed to handle multiple data streams simultaneously and may include provisions for data filtering and validation.

The real-time display interface (76) may employ various visualization technologies to present physiological data to medical practitioners. The interface may incorporate multiple display modes and may feature customizable layouts. The system may be designed to present critical information clearly and may include provisions for alert generation and display.

The patient positioning tracker (77) may utilize various technologies to monitor patient location and orientation. The tracking system may incorporate multiple reference points and may feature continuous monitoring capabilities. The system may be designed to maintain accurate position information and may include provisions for automated adjustment of sensor alignment.

The integration and safety systems (80) encompass multiple safeguards, including an emergency shutdown mechanism (81), water chemistry monitoring (82), and environmental controls (83). A sterilization system (84) maintains hygiene standards, while the power management system (85) ensures consistent operation. The data transmission system (86) facilitates information flow, supported by a backup power supply (87) for uninterrupted operation.

The emergency shutdown mechanism (81) may incorporate various technologies designed to rapidly and safely terminate system operation when required. The mechanism may utilize multiple triggering methods and may feature redundant shutdown pathways. The system may be designed to maintain safe conditions during shutdown and may include provisions for both automated and manual activation.

The water chemistry monitoring system (82) may employ various analytical technologies to assess water quality parameters. The monitoring system may incorporate multiple sensor types and may feature continuous sampling capabilities. The system may be designed to track various chemical parameters and may include provisions for automated adjustment of water chemistry.

The environmental controls (83) may utilize various technologies to maintain optimal conditions within the treatment chamber. The control system may incorporate multiple environmental parameters and may feature interactive adjustment capabilities. The system may be designed to maintain stable conditions and may include provisions for rapid response to environmental changes.

The sterilization system (84) may employ various decontamination technologies to maintain hygienic conditions. The system may incorporate multiple sterilization methods and may feature automated cycling capabilities. The sterilization mechanism may be designed to maintain aseptic conditions and may include provisions for verification of effectiveness.

The power management system (85) may utilize various technologies to control and distribute electrical power throughout the device. The system may incorporate multiple power conditioning stages and may feature surge protection capabilities. The management system may be designed to provide stable power delivery and may include provisions for power quality monitoring.

The data transmission system (86) may employ various communication technologies to facilitate information flow between system components; in a preferred embodiment, system (86) may be managed autonomously by artificial intelligence integrated thereto. The transmission system may incorporate multiple communication protocols and may feature secure data transfer capabilities. The system may be designed to maintain reliable communications and may include provisions for data integrity verification.

The backup power supply (87) may utilize various technologies to maintain system operation during primary power interruptions. The supply system may incorporate multiple power sources and may feature automatic switching capabilities. The system may be designed to maintain critical functions and may include provisions for orderly system shutdown when required. In one alternative embodiment, the lid of the device may be manually opened, wherein shock absorbers may assist in manually opening the lid in the event of an emergency.

In operation, the system provides a controlled environment where patients float in the water containment vessel (31) while receiving precisely targeted shock wave therapy. The AI control system (60) continuously optimizes treatment parameters based on real-time patient data from the Infinitus Omni Remote Sensor System (70), while the robotic arm assembly (40) delivers treatment with precise positioning and timing. The integration of these systems enables a novel approach to shock wave therapy that combines the benefits of sensory deprivation with advanced treatment delivery and monitoring capabilities.

Exemplary Operation of the Shockwave Therapy System

In an exemplary operation of the present invention, a patient may first be introduced to the treatment chamber through the entry/exit assistance mechanism (25). Upon entry, the patient may be assisted into the water containment vessel (31) where the salinity control mechanism (33) may have established optimal flotation conditions. Once the patient achieves a stable floating position, the Infinitus Omni Remote Sensor System (70) may begin monitoring vital signs through its radar-based monitor (72), infrared thermometry system (73), and remote pulse oximetry system (74). The real-time display interface (76) may present these physiological parameters to the attending medical practitioners. The AI control system (60) may then initiate a pretreatment assessment phase where the patient positioning detection system (62) may establish the patient's baseline position. The treatment optimization algorithm (61) may develop an initial treatment protocol based on the patient's specific condition and physiological parameters. The robotic arm assembly (40) may then position its articulating arms (41) according to the predetermined treatment map. The shock wave generation system (50) may initiate therapy delivery through its emission units (46), with the wave focusing mechanism (52) directing therapeutic energy to targeted treatment areas. Throughout the treatment session, the movement prediction system (64) may anticipate and compensate for any patient movement, while the real-time treatment adjustment mechanism (63) may modify treatment parameters based on continuous feedback from the sensor systems. The treatment pattern recognition system (65) may analyze therapeutic responses to optimize ongoing treatment delivery. The environmental control system (83) may maintain stable conditions within the chamber while the water chemistry monitoring system (82) may ensure optimal water parameters. The sterilization system (84) may operate continuously to maintain hygienic conditions. Upon completion of the therapeutic session, the system may initiate a controlled shutdown sequence where the robotic arms may return to their home positions and the entry/exit assistance mechanism (36) may facilitate safe patient egress from the flotation system. Throughout the entire process, the integration and safety systems (80) may monitor all operational parameters to ensure safe and effective treatment delivery.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A shockwave therapy chamber, comprising:

a) a sensory deprivation chamber;

b) a body of water contained within said sensory deprivation chamber, said body of water configured to support a floating user and to optimize propagation and transmission of shockwaves therethrough for enhanced treatment efficacy;

c) a plurality of robotic arms positioned within said sensory deprivation chamber and configured to deliver targeted shock wave therapy while maintaining predetermined distances from the floating user;

d) a shock wave generation system operatively coupled to said plurality of robotic arms for delivering directed shock wave therapy to said floating user through said body of water;

e) an artificial intelligence computer system operatively connected to said plurality of robotic arms, said artificial intelligence computer system configured to:

a) receive an uploaded full body scan of the floating user;

b) perform diagnostics on the full body scan to identify injuries;

c) create a treatment plan based on the identified injuries;

d) customize the treatment plan to the floating user's needs and requirements; and e) optimize the treatment plan in real-time by collecting vital sign data and modifying shock wave therapy parameters based on said vital sign data;

f) a remote sensor system, said remote sensor system configured to monitor vital signs without physical contact with the floating user and to provide said vital sign data to said artificial intelligence computer system.

2. The shock wave therapy system of claim 1, wherein said sensory deprivation chamber comprises: a light isolation system; a sound dampening system; a temperature control system; and an entry/exit assistance mechanism.

3. The shock wave therapy system of claim 1, further comprising: a water containment vessel; a water filtration system; a salinity control mechanism; and a water temperature regulation system.

4. The shock wave therapy system of claim 1, wherein said plurality of robotic arms comprises: waterproof arm housings; joint actuators; position sensors; and shock wave emission units.

5. The shock wave therapy system of claim 1, wherein said shock wave generation system comprises: a wave focusing mechanism; an intensity control system; a wave frequency modulator; and an energy distribution system.

6. The shock wave therapy system of claim 1, wherein said artificial intelligence control system comprises: a treatment optimization algorithm; a patient positioning detection system; a movement prediction system; and a treatment pattern recognition system.

7. The shock wave therapy system of claim 1, wherein said remote sensor system comprises: a radar-based vital sign monitor; an infrared thermometry system; a remote pulse oximetry system; and a real-time display interface.

8. The shock wave therapy system of claim 1, further comprising: an emergency shutdown mechanism; a water chemistry monitoring system; a sterilization system; and a backup power supply.

9. The shock wave therapy system of claim 1, wherein said sensory deprivation chamber comprises a double-wall construction filled with sound-dampening material.

10. A shockwave therapy system comprising:

a sensory deprivation chamber comprising a light isolation system, a sound dampening system, and a temperature control system;

a flotation system within said sensory deprivation chamber, said flotation system comprising a water containment vessel, a water filtration system, a salinity control mechanism, and a water temperature regulation system, wherein said flotation system is configured to support a user in a floating position and to optimize propagation and transmission of shockwaves through water therein for enhanced treatment efficacy;

a plurality of waterproof robotic arms positioned within said sensory deprivation chamber, each robotic arm comprising joint actuators, position sensors, and a shock wave emission unit configured to deliver targeted shock wave therapy while maintaining predetermined distances from the floating user;

a shock wave generation system operatively coupled to said plurality of robotic arms, said shock wave generation system comprising a wave focusing mechanism, an intensity control system, a wave frequency modulator, and an energy distribution system for delivering directed shock wave therapy to the floating user through said water;

a remote sensor system mounted at the top of said sensory deprivation chamber, said remote sensor system comprising a radar-based vital sign monitor, an infrared thermometry system, a remote pulse oximetry system, and a real-time display interface for monitoring vital signs without physical contact with said user and providing vital sign data;

an artificial intelligence control system operatively connected to said plurality of robotic arms and said remote sensor system, said artificial intelligence control system comprising a treatment optimization algorithm, a patient positioning detection system, a real-time treatment adjustment mechanism, and a movement prediction system configured to:

a) receive an uploaded full body scan of the floating user;

b) perform diagnostics on the full body scan to identify injuries;

c) create a treatment plan based on the identified injuries;

d) customize the treatment plan to the floating user's needs and requirements; and e) optimize the treatment plan in real-time by collecting said vital sign data and modifying shock wave therapy parameters based on said vital sign data; and an integration and safety system comprising an emergency shutdown mechanism, a water chemistry monitoring system, a sterilization system, and a backup power supply.

11. The shockwave therapy system of claim 1, wherein said body of water is configured to optimize the propagation and transmission of shockwaves, thereby enhancing the efficacy of treatment delivery.

12. A shockwave therapy chamber, comprising:

a sensory deprivation chamber;

a body of water contained within the sensory deprivation chamber, the body of water configured to support a floating user and to optimize the propagation and transmission of shockwaves for enhanced treatment efficacy;

a plurality of robotic arms positioned within the sensory deprivation chamber, the robotic arms configured to deliver targeted shock wave therapy while maintaining predetermined distances from the floating user;

a shock wave generation system operatively coupled to the robotic arms for delivering directed shock wave therapy to the floating user through the body of water;

an artificial intelligence computer system operatively connected to the robotic arms, the artificial intelligence computer system configured to:

a) receive an uploaded full body scan of the floating user;

b) perform diagnostics on the full body scan to identify injuries;

c) create a treatment plan based on the identified injuries;

d) customize the treatment plan to the floating user's needs and requirements; and e) optimize the treatment plan in real-time by collecting vital sign data and modifying shock wave therapy parameters based on the vital sign data;

and a remote sensor system configured to monitor vital signs without physical contact with the floating user and to provide the vital sign data to the artificial intelligence computer system.

13. A shockwave therapy chamber, comprising:

a sensory deprivation chamber;

a body of water contained within the sensory deprivation chamber, the body of water configured to support a floating user and to optimize the propagation and transmission of shockwaves for enhanced treatment efficacy;

a plurality of robotic arms positioned within the sensory deprivation chamber, the robotic arms configured to deliver targeted shock wave therapy while maintaining predetermined distances from the floating user;

a shock wave generation system operatively coupled to the robotic arms for delivering directed shock wave therapy to the floating user through the body of water;

a remote sensor system configured to monitor vital signs without physical contact with the floating user and to provide the vital sign data; and an artificial intelligence computer system operatively connected to the robotic arms and the remote sensor system, the artificial intelligence computer system configured to:

a) receive an uploaded full body scan of the floating user;

b) perform diagnostics on the full body scan to identify injuries;

c) create a treatment plan based on the identified injuries;

d) customize the treatment plan to the floating user's needs and requirements; and e) optimize the treatment plan in real-time by modifying shock wave therapy parameters based on the vital sign data.

14. A shockwave therapy chamber, comprising:

a sensory deprivation chamber;

a body of water contained within the sensory deprivation chamber, the body of water configured to support a floating user and to optimize the propagation and transmission of shockwaves for enhanced treatment efficacy;

a plurality of robotic arms positioned within the sensory deprivation chamber, the robotic arms configured to deliver targeted shock wave therapy while maintaining predetermined distances from the floating user;

a shock wave generation system operatively coupled to the robotic arms for delivering directed shock wave therapy to the floating user through the body of water;

a remote sensor system configured to monitor vital signs without physical contact with the floating user and to provide the vital sign data; and an artificial intelligence computer system operatively connected to the robotic arms and the remote sensor system, the artificial intelligence computer system configured to:

a) receive an uploaded full body scan of the floating user;

b) perform diagnostics on the full body scan to identify injuries;

c) create a treatment plan based on the identified injuries;

d) customize the treatment plan to the floating user's needs and requirements; and e) modify shock wave therapy parameters in real-time based on the vital sign data provided by the remote sensor system.

* * * * *